United States Patent
Redhead et al.

(10) Patent No.: US 8,709,437 B2
(45) Date of Patent: Apr. 29, 2014

(54) CLOSTRIDIUM CHAUVOEI POLYPEPTIDE, DNA ENCODING THE POLYPEPTIDE AND A VACCINE COMPRISING THE POLYPEPTIDE

(75) Inventors: Keith Redhead, Milton Keynes (GB); Joachim Frey, Bern (CH); Edy M. Vilei, Bern (CH); Andreas Walter Claudius Rohwer, Schwabenheim (DE); Anders Johansson, Bern (CH)

(73) Assignees: Intervet International B.V., Boxmeer (NL); Universitat Bern, Bern (CH)

( * ) Notice: Subject to any disclaimer, the term of this patent is extended or adjusted under 35 U.S.C. 154(b) by 0 days.

(21) Appl. No.: 13/145,882

(22) PCT Filed: Jan. 28, 2010

(86) PCT No.: PCT/EP2010/050972
§ 371 (c)(1),
(2), (4) Date: Jul. 22, 2011

(87) PCT Pub. No.: WO2010/086353
PCT Pub. Date: Aug. 5, 2010

(65) Prior Publication Data
US 2011/0280900 A1    Nov. 17, 2011

Related U.S. Application Data

(60) Provisional application No. 61/148,512, filed on Jan. 30, 2009.

(30) Foreign Application Priority Data

Jan. 30, 2009    (EP) ..................................... 09151763

(51) Int. Cl.
*A61K 39/08*    (2006.01)
*G01N 33/566*    (2006.01)
*C07K 14/33*    (2006.01)
*C07K 16/12*    (2006.01)

(52) U.S. Cl.
USPC ........................................ 424/190.1; 530/350

(58) Field of Classification Search
None
See application file for complete search history.

(56) References Cited

U.S. PATENT DOCUMENTS

2010/0291131 A1*   11/2010   Moore et al. ............... 424/190.1

OTHER PUBLICATIONS

Colman (Res. Immunology, Jan. 1994, vol. 145, pp. 33-36).*
Greenspan et al. (Nature Biotechnology 7: 936-937, 1999).*
Bendtsen et al. "Improved Prediction of Signal Peptides: SignalP 3.0", (2004) J. Mol. Biol. 340:783-795.
Frey et al. "Purification and Partial Characterization of a Hemolysin Produced by *Actinobacillus pleuropneumoniae* Type Strain 4074", (1988) FEMS Microbiology Letters 55:41-46.
Hang'Ombe et al. "Purification and Sensitivity of *Clostridium chauvoei* Hemolysin to Various Erythrocytes", (2006) Comparative Immunology, Microbiology & Infectious Diseases 29:263-268.
Hunter et al. "Molecular Genetic Analysis of Beta-Toxin of *Clostridium perfringens* Reveals Sequence Homology with Alpha-Toxin, Gamma-Toxin, and Leukocidin of *Staphylococcus aureus*" (Sep. 1993) Infection and Immunity 61(9):3958-3965.
Keyburn et al. "NetB, a New Toxin That Is Associated with Avian Necrotic Enteritis Caused by *Clostridium perfringens*" (Feb. 2008) PLoS Pathogens 4(2)e26:0001-00011.
Kijima-Tanaka et al. "Protection of Mice Against *Clostridium chauvoei* Infection by Anti-Idiotype Antibody to a Monoclonal Antibody to Flagella", (1994) FEMS Immunology and Medical Microbiology 8:183-188.
Laemmli et al. "Cleavage of Structural Proteins During the Assembly of the Head of Bacteriophage T4", (Aug. 15, 1970) Nature, 227:680-685.
Nagano et al. "Human Fulminant Gas Gangrene Caused by *Clostridium chauvoei*" (Apr. 2008) Journal of Clinical Microbiology 46(4):1545-1547.
Pilo et al. "A Metabolic Enzyme as a Primary Virulence Factor of *Mycoplasma mycoides* subsp. *mycoides* Small Colony" (Oct. 2005) Journal of Bacteriology 187(19):6824-6831.
Pitcher et al. "Rapid Extraction of Bacterial Genomic DNA with Guanidium Thiocyanate" (1989) Letters in Applied Microbiology 8:151-156.
Song et al. "Structure of Staphylococcal α-Hemolysin, a Heptameric Transmembrane Pore" (Dec. 1996) Science 274:1859-1866.
Tamura et al. "Partial Characterization of the Hemolysin Produced by *Clostridium chauvoei*", (1992) J. Vet. Med. Sci. 54(4):777-778.
Useh et al. "Pathogenesis and Pathology of Blackleg in Ruminants: The Role of Toxins and Neuraminidase" (2003) Veterinary Quarterly 25(4):155-159.
Walker et al. "Restoration of Pore-forming Activity in Staphylococcal α-Hemolysin by Targeted Covalent Modification" (1995) Protein Engineering 8(5):491-495.
International Search Report corresponding to PCT/EP2010/050972, mailed Mar. 31, 2010.

* cited by examiner

Primary Examiner — Robert A Zeman

(57) ABSTRACT

The present invention pertains to the identification and initial characterization of CctA, a novel, secreted toxin of *Clostridium chauvoei* that represents the major cytotoxic activity of *C. chauvoei*. This toxin confers *C. chauvoei* its characteristic strong hemolytic activity towards erythrocytes of various species, since anti-CctA antibodies fully neutralize hemolysis by *C. chauvoei* on standard blood-agar medium or in cell-free supernatants of liquid cultures.

5 Claims, 3 Drawing Sheets

Figure 3

Figure 1:
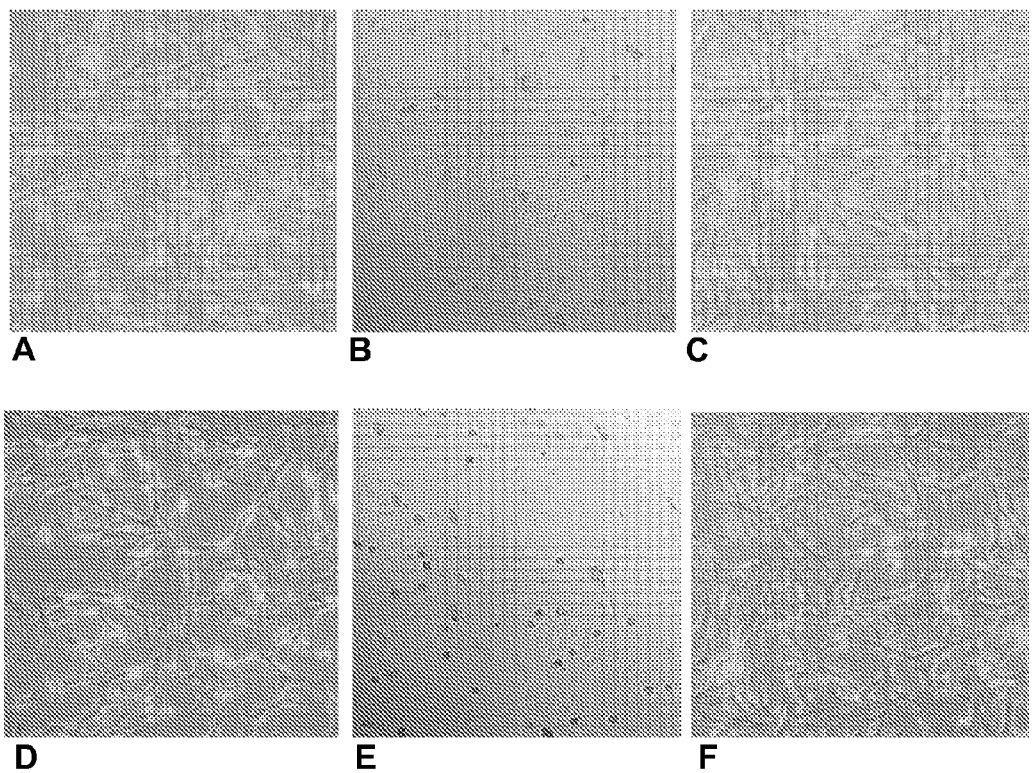

CLOSTRIDIUM CHAUVOEI POLYPEPTIDE, DNA ENCODING THE POLYPEPTIDE AND A VACCINE COMPRISING THE POLYPEPTIDE

CROSS-REFERENCE TO RELATED APPLICATIONS

This application is a national stage entry under 35 U.S.C. §371 of PCT/EP2010/050972, filed on Jan. 28, 2010, which claims priority to U.S. Provisional Application No. 61/148,512, filed on Jan. 30, 2009, and EP Application No. 09151763.1, filed on Jan. 30, 2009. The content of PCT/EP2010/050972 is hereby incorporated by reference in its entirety.

The present invention pertains to *Clostridium chauvoei*, an anaerobic Gram-positive bacterium which is the pathogenic agent of blackleg, a wide spread severe disease causing serious toxaemia and high mortality of, particularly, cattle and also sheep and other domestic animals. *C. chauvoei* is one of the most important pathogenic *Clostridium* species causing considerable losses in livestock production. Although, *C. chauvoei* infections are specifically found in ruminants, a fatal case of human fulminant gas gangrene caused by *C. chauvoei* has been reported (Nagano, N. et al, 2008: "Human fulminant gas gangrene caused by *Clostridium chauvoei*" in J. Clin. Microbiol., 46, 1545-1547). Blackleg in cattle and sheep is controlled by commercial vaccines consisting of whole formalinized bacteria and culture supernatant, generally presented as polyvalent formulations. However, the particular antigens necessary to induce protective immunity against blackleg are unknown, thus requiring expensive and work-intensive animal models for potency testing of vaccine batches or determination of severity of infection of an individual animal (including humans). Design of novel vaccines, in vitro potency tests and diagnostic tests are mainly hampered by the lack of basic knowledge on the molecular mechanisms of pathogenicity of *C. chauvoei*. Ruminants are exposed to the pathogen by ingestion of *C. chauvoei* spores present in the soil which then propagate in the host and produce potent toxins that are assumed to induce in the target host cells necrosis, oedemic lesions, fever and subsequently lameness and death of the animals. Currently, five different toxins are postulated in *C. chauvoei* including an oxygen-stable hemolysin, oxygen-labile hemolysin, DNase, hyaluronidase and neuraminidase (Hang'ombe, B. M. et al, 2006, "Purification and sensitivity of *Clostridium chauvoei* hemolysin to various erythrocytes" in Comp. Immunol. Microbiol. Infect. Dis. 29, 263-268; further referred to as Hang'ombe, 2006). A 27 kDa protein with hemolytic activity towards erythrocytes of cattle, sheep and chicken was recently purified from *C. chauvoei* strain C6 H without specifying, whether it represents the oxygen-stabile or the oxygen labile hemolysin nor characterizing the protein any further (Hang'ombe, 2006).

It is an object of the present invention to overcome or at least mitigate the disadvantages of the prior art. To this end a novel polypeptide has been found, which polypeptide represents the major cytotoxic activity of *C. chauvoei*. This polypeptide in its naturally occurring toxic form (tentatively called "*Clostridium chauvoei* toxin A" or "CctA") confers *C. chauvoei* its characteristic strong hemolytic activity towards erythrocytes. The novel polypeptide is defined by its property that it binds to polyclonal rabbit antibodies raised against a protein according to SEQ ID NO 1. This polypeptide enables the design of a novel vaccine to treat an infection with *C. chauvoei*, and adequate potency and diagnostic tests. For this, the polypeptide may be purified, i.e. impurities may be removed from it, e.g. by a specific increase of its concentration relative to the concentration of other soluble polypeptides in a mixture with the present polypeptide, or by specific scavenging of other polypeptides in such a mixture. The polypeptide may be in an active form (toxic) or in an inactivated form (non or at least less toxic when compared to its natural occurring counterpart).

In an embodiment the polypeptide is expressed recombinantly, i.e. expressed as a result of genetic engineering, which engineering leads to a combination of genes not present in naturally occurring organisms. This way, the polypeptide can be arrived at in a dedicated fashion, thus enabling the provision of a constitution that comprises in essence only the polypeptide of the present invention, or at least no other polypeptides that correspond to *C. chauvoei* polypeptides.

In another embodiment, the polypeptide is fused to a carrier protein. This way, advantageous properties can be added to the polypeptide or negative properties can be masked. For example, the carrier protein can be used to make the polypeptide less toxic or even non-toxic, may be used to alter the solubility of the polypeptide or may be used to facilitate expression of the polypeptide. In a preferred embodiment the carrier protein contains B- or T-cell epitopes, for example to enhance the immunogenic properties of the polypeptide. A NusA protein (N utilisation substance protein A, a transcription termination-antitermination factor) has proven to be a good example of a carrier protein. The NusA provides the polypeptide according to the invention a good solubility in aqueous media.

In another embodiment the polypeptide according to the present invention comprises the polypeptide according to SEQ ID NO 1. In a further embodiment, the polypeptide according to the present invention is the protein according to SEQ ID NO 1 or SEQ ID NO 2.

The present invention also pertains to DNA that encodes a polypeptide as described here-above. The DNA may be purified, i.e. taken out of its natural chromosome, for example isolated as a separate entity. In that case it may be placed in genome of different species using genetic engineering techniques to arrive at recombinant DNA. In an embodiment, the DNA comprises the DNA according to SEQ ID NO 3 or SEQ ID NO 4, or is even restricted to DNA according to those sequence identifiers.

The present invention also pertains to a vaccine to treat an infection caused by *Clostridium chauvoei*, wherein the vaccine comprises a polypeptide as described here-above and a pharmaceutically acceptable carrier for the polypeptide. A vaccine in the sense of this invention is a constitution suitable for application to an animal (including humans), comprising one or more antigens in an immunologically effective amount (i.e. capable of stimulating the immune system of the target animal sufficiently to at least reduce the negative effects of a challenge with a wild-type micro-organism), typically combined with a pharmaceutically acceptable carrier and optionally comprising immunostimulating agents (adjuvants), which upon administration to the animal induces an immune response in that animal for (aiding in) preventing, ameliorating or curing the disorder arising from the infection with *C. chauvoei*. A pharmaceutically acceptable carrier can be any solvent, dispersion medium, coating, antibacterial and antifungal agent, isotonic and absorption delaying agent, or other material that is physiologically compatible with and acceptable for the target animal, e.g. by being made i.a. sterile. Some examples of such carrying media are water, saline, phosphate buffered saline, bacterium culture fluid, dextrose, glycerol, ethanol and the like, as well as combinations thereof. They may provide for a liquid, semi-solid and solid dosage form, depending on the intended mode of administration. As is commonly known, the presence of a carrying medium is not essential to the efficacy of a vaccine, but it may significantly simplify dosage and administration of the antigen. In general, a vaccine can be manufactured by using art-known methods that basically comprise admixing the antigens (or a composition containing the antigens) with the pharmaceutically acceptable carrier. As mentioned, other substances such as adjuvants, stabilisers, viscosity modifiers or other components may be added to the vaccine depending on the intended use or required properties of the vaccine. For parenteral or oral vaccination many forms are suitable, in particular liquid formulations (with dissolved, emulsified or suspended antigens) but also solid formulations such as implants or an intermediate form such as a solid carrier for the antigen suspended in a liquid. Vaccines and suitable (physical) forms for these vaccines have been known for more than 200 years.

In an embodiment the vaccine additionally comprises a hyaluronidase or sialidase polypeptide (which also covers the combined addition of these polypeptides). As commonly known (i.a. described in Hang'ombe 2006), *C. chauvoei* produces a hyaluronidase. Applicant found that *C. chauvoei* also produces a sialidase. The efficacy of a vaccine to treat an infection with *C. chauvoei* may be increased by adding a hyaluronidase or sialidase polypeptide (including a combination of such polypeptides). In this sense a hyaluronidase polypeptide is a polypeptide being or derived from a hyaluronidase (for example a toxoided polypeptide), having the ability to induce antibodies directed to, at least partly, neutralise the toxic effect of a hyaluronidase produced by a wild type *C. chauvoei* bacterium. A sialidase polypeptide in this sense is a polypeptide being or derived from a sialidase (for example a toxoided polypeptide), having the ability to induce antibodies directed to, at least partly, neutralise the toxic effect of a sialidase produced by a wild type *C. chauvoei* bacterium.

The present invention also pertains to antibodies raised against a polypeptide as described here-above, for example as an acute treatment against blackleg, but in particular for determining the amount of *Clostridium chauvoei* corresponding polypeptide in a sample. Since the polypeptide according to the present invention represents the major cytotoxic activity of *C. chauvoei*, antibodies directed against it are ideally suitable for determining the *C. chauvoei* activity of various constitutions such as a vaccine to treat an infection with *C. chauvoei* or a volume of body fluid, in particular serum. In the latter case, the use could be directed to determine infection with the bacterium or even the severity of that infection. The use of antibodies to determine amounts of polypeptides in various fluids is commonly known in the art and can for example be embodied in the form of an ELISA test (enzyme-linked immunosorbent assay).

The invention will be further explained using the following examples.

MATERIALS AND METHODS

Strains and Culture Conditions

*C. chauvoei* strains isolated from blackleg of cattle from various parts of the world and the type strain as well as the *Escherichia coli* strain used in this study are listed in table 1.

TABLE 1

| Strain | species | original nr. | description |
|---|---|---|---|
| JF703 | *E. coli* | BL21 (DE3) | (F−, ompT, hsdSB, ($r_B^-$, $m_B^-$), DE3 [λDE3 i21I lacI lacUV5 lacZ T7-RNA-pol. (lysogenic), int−] |
| JF1863 | *C. chauvoei* | ATCC10092 | type strain |
| JF2696 | *C. chauvoei* | SP | isolated from cattle with blackleg, Brazil, 2002 |
| JF3703 | *C. chauvoei* | CC4 (665) | UK strain, obtained from the Weybridge Collection in 1956 |
| JF3840 | *C. chauvoei* | M78:45/4/ E8.10.65 | isolated from cattle with blackleg, Switzerland, 1965 |
| JF4135 | *C. chauvoei* | C6 O/D 1126/04 | isolated from cattle with virulent blackleg, Switzerland, 2004 |
| JF4251 | *C. chauvoei* | AN 2548/02 | isolated from cattle with blackleg, Sweden, 2002 |
| JF4253 | *C. chauvoei* | AN 2500/07 | isolated from cattle with blackleg, Sweden, 2007 |

*C. chauvoei* was grown on Tryptic Soy Agar medium containing 5% sheep erythrocytes (bioMérieux, Genève, Switzerland) or in liquid Cooked Meat Medium (CMM) (Oxoid, Basingstoke, UK) at 37° C. for 72 hours unless specifically noted. *Escherichia coli* strains were grown on Luria-Bertani (LB) broth of LB agar at 37° C. Ampicillin (100 μg/ml) was added for selection of recombinant plasmids.

DNA Extraction, DNA Manipulation

DNA from *C. chauvoei* strains was extracted by the guanidium thiocyanate method (Pitcher, D. G. et al., 1989, "Rapid extraction of bacterial genomic DNA with guanidium thiocyanate" in Lett. Appl. Microbiol. 8, 151-156) followed by 2 phenol extractions and ethanol precipitation. Restriction enzyme digestion, ligation, transformation, plasmid extraction, agarose gel electrophoresis and isolation of DNA fragments were performed using standard methods (Ausubel, F. M. et al., 1999: Current protocols in molecular biology. John Wiley & Sons, Inc., New York).

Expression and Purification of Recombinant CctA and Production of Rabbit Anti-CctA Antiserum SEQ ID NO 4 shows the full DNA sequence of the cctA gene. The part of the cctA gene containing the CctA toxin without the signal sequence (SEQ ID NO 3) was amplified by PCR using the oligonucleotide primers CCTO2AL (ttc-cccggggcAGTGAA GGAGTAAAGACTTTTA) (SEQ ID NO 5) and CCTO2AR (ttgcggccgcTTAATATCCTGCAT-GCTCAA CAG) (SEQ ID NO 6) (nucleotides in lower cases were added to create SmaI and NotI restriction sites respectively and supplementary added nucleotides) and Pwo DNA-polymerase with proofreading activity. The PCR fragment was purified, cut with restriction enzymes SmaI and NotI and cloned into the SmaI and NotI restriction sites of expression vector pET-43.1a (Novagen, Gibbstown, N.J., United States) in order to create a recombinant plasmid for the expression of poly-His tagged CctA:NusA fusion protein. The recombinant plasmid was sequenced in order to insure the correct construct and subsequently transferred by transformation into *E. coli* strain BL21 (DE3) for expression. An empty vector pET-43.1a (Novagen) was also transformed separately to *E. coli* BL21 (DE3) to express poly-His tagged NusA as control peptide. Recombinant poly-His tagged CctA:NusA and NusA were expressed in BL21 (DE3) after induction of bacterial cultures with 0.1 mM IPTG at mid exponential growth at 37° C. and subsequent incubation at 37° C. for 2 hours. Purification of the poly-His tagged protein was done on a nickel affinity column (Qiagen, Basel, Switzerland) from guanidium thiocyanate lysed bacterial cultures with a pH gradient for elution according to the manufacturer and extensive dialysis of the corresponding fractions against 50 mM phosphate buffer pH 7.5 plus 144 mM NaCl (PBS). NusA-poly-His appeared as a 70 kDa and CctA:NusA-poly-His as a 102 kDa protein on SDS PAGE control gels. Protein solutions of these two recombinants were adjusted to 200 μg/ml and stocked at −80° C. until use. The CctA polypeptide part of the fusion protein arrived at is depicted in SEQ ID NO 1. The full protein sequence of the pretoxin (including the Val Gln Ala Gln Glu signal peptidase recognition site, a.a. 27-31) is depicted in SEQ ID NO 2.

Rabbit antiserum directed against CctA can be obtained as follows. An experimental vaccine is prepared by blending the protein solution of recombinant CctA as referred to here-above with 25% v/v Alhydrogel (available from Brenntag Biosector, Frederikssund, Denmark) to produce a vaccine with a final concentration of 50 μg of recombinant protein per ml.

Three female SPF rabbits, after approximately one month's acclimatisation in their housing, are each bled from the ear (approximately 1 ml blood from each rabbit). Immediately after that they are vaccinated i.m. with 1.0 ml of the experimental vaccine (0.5 ml into each rear thigh). Two weeks later each rabbit is vaccinated sub-cutaneously with two 0.5 ml doses of the vaccine at different sites. Then two weeks later each rabbit is vaccinated sub-cutaneously again with two 0.5 ml doses of the same vaccine, again at different sites. Two weeks after the third vaccination the rabbits are bled from the heart under terminal anaesthesia. Sera are separated from the blood samples. An equal amount of each of the three sera is mixed to give a serum pool. To remove the antibodies directed against the NusA part of the fusion protein, the pooled serum is decomplemented by incubating at 58° C. for 10 minutes. Subsequently the anti-CctA:NusA rabbit antiserum is absorbed twice with recombinant NusA-poly-His by incubating 1 ml serum with 70 μl NusA-poly-His (200 μg/ml) for 1 h with constant mild shaking at 37° C. followed by centrifugation at 15'000×g for 30 min at 4° C. to precipitate the NusA antigen-antibody complexes. Absorbed serum is tested by immunoblot containing recombinant CctA:NusA and NusA (the serum shows no visible reactions with recombinant NusA peptide) and is referred to as rabbit polyclonal anti-CctA antibodies. The serum is stored at a temperature below minus 15° C.

Immuno Blot Analysis of *C. chauvoei* Strains and Culture Supernatants

Culture supernatant and sedimented bacteria of *C. chauvoei* grown in CMM for 24 h, 48 h and 92 h were obtained by centrifugation at 10,000×g for 30 min. Sedimented bacteria were suspended in PBS buffer in the same volume as the original culture. Aliquots of 15 μl of suspended bacteria or culture supernatants (containing secreted proteins) were analyzed by sodiumdodecyl sulfate-polyacrylamide gel electrophoresis (PAGE) on 12% polyacrylamide gels under reducing and non-reducing conditions (Laemmli, U.K., 1970, "Cleavage of structural proteins during the assembly of the head of bacteriophage T4" in Nature 227, 680-685). The proteins separated by PAGE were transferred to nitrocellulose membranes (BioRad Laboratories, Hercules, USA). The membranes were blocked by incubation for 12 h in 1% blocking buffer, washed and then incubated with rabbit polyclonal antibodies as described here-above, diluted 1:1000 in blocking buffer followed by incubation with alkaline phosphatase lconjugated goat anti-rabbit IgG heavy and light chains (Kirkegaard & Perry Laboratories, Gaithersburg, Md., USA) diluted 1:2000 in blocking buffer for 90 min and then reacted with the chromogenic substrate 5-bromo-4-chloro-3-indolyl phosphate/nitroblue tetrazolium (BCIP/NBT) (Sigma Aldrich, St. Louis, Mo., USA) according to the [[suppliers]] supplier's instructions (Roche, Rotkreuz, Switzerland). A reaction is positive (i.e. the subject polypeptide binds to the polyclonal rabbit antibodies) if a band is visible with the naked human eye.

Cell Lines, Hemolysis and Cytotoxicity Assay

Embryonic calf nasal epithelial (ECaNEp) cells (#270, passage 7) were grown in MEM-Earl medium in 24-well microtiter plates containing 0.5 ml MEM-Earl medium in a humidified environment of 5% $CO_2$ at 37° C. To test for cytotoxicity, the cells were cultured to approximately 10% confluence reading 50,000 cells per well. Supernatant of *C. chauvoei* cultures or recombinant purified CctA:NusA protein or recombinant NusA produced in the same *E. coli* host from the empty cloning vector pET-43.1 a was added to the medium in two fold steps until a final dilution of 1:256 respectively until 0.4 μg/ml purified protein in PBS buffer and incubated for up to 16 h in 5% $CO_2$ at 37° C. The cells were photographed by phase-contrast microscopy at various times after the additions. Morphologically intact ECaNEp cells were counted after fixation and staining with a solution of 0.75% crystal violet, 0.25% NaCl, 1.75% formaldehyde, 50% ethanol and photographed by phase-contrast microscopy as described previously (Pilo, P. et al., 2005: "A metabolic enzyme as a primary virulence factor of *Mycoplasma mycoides* subsp. *mycoides* Small Colony" in J. Bacteriol. 187, 6824-6831). For neutralization experiments, culture supernatant diluted to 1:32 or recombinant CctA:NusA at 10 μg/ml were mixed with polyclonal decomplemented rabbit anti CctA serum or decomplemented serum taken before immunization (control) at various dilutions ranging from 1:2 until 1:128, incubated for 15 min at 20° C. and then added to the ECaNEp cell cultures for cytotoxicity analysis as described above.

Hemolytic activity towards sheep erythrocytes was measured as described before (Frey, J. et al., 1988: "Purification and partial characterization of a hemolysin produced by *Actinobacillus pleuropneumoniae* type strain 4074" in FEMS Microbiol. Lett. 55, 41-46) using culture supernatants of strain JF4135 or purified recombinant CctA:NusA at various concentrations.

Guinea Pig Protection Assay

Ten Guinea pigs are divided randomly into 2 groups of 5 animals. One group is left as control. In the other group, each animal receives one dose of 1.0 ml of the test vaccine subcutaneously in the flank. Twenty-eight days after the first injection, each animal in the test group receives a second injection with the test vaccine subcutaneously in the opposite flank. Fourteen days following the second injection all animals are challenged with a suspension of viable *Clostridium chauvoei* spores strain JF3703 (0.5 ml) in 4% $CaCl_2$ solution, injected intramuscularly into one of the rear thighs. The Guinea pigs are observed four times a day following challenge for a period of 5 consecutive days. Pigs showing deeply coloured (purple/black) swollen legs extending outwards along the flank, or paleness of the face (around the lips and eyes), or stiffness in the whole body, or reluctance to move in the cage (not even seeking shelter) will be deemed moribund and are euthanized.

In a first experiment a vaccine is used as described here-above, containing 50 μg of the recombinant CctA:NusA protein per ml. In a second experiment a corresponding vaccine is used, differing only in the amount of recombinant protein namely 70 μg per ml. In this second experiment, each pig receives 2 ml per vaccination (instead of 1 ml as is the case in the first experiment).

Results

Identification of a Novel Toxin Gene CctA in the *C. Chauvoei* Genome The newly found polypeptide in its naturally occurring toxic form appears to be a highly structured porin and designated "Clostridium chauvoei toxin A" (abbreviated to CctA) and its corresponding gene cctA. The gene cctA contains a strong potential promoter sequence [−10 and −35 box] 187 nucleotides (n.t.) upstream the ATG start codon of the open reading frame (ORF) of cctA (see SEQ ID NO 4). A ribosome binding site (GGGAGGG) is located 6 n.t. upstream the start codon ATG of cctA which encodes 317 a.a. of the pre-toxin of CctA with a signal peptide region of 29 residues as described by SignalP (Bendtsen, J. D. et al., 2004: "Improved prediction of signal peptides: SignalP 3.0" in J. Mol. Biol. 340, 783-795). The molecular mass of the mature CctA toxin, calculated from the deduced 288 a.a. is 32.3 kDa and the pI (isoelectric point) is 5.47. It shows weak similarity to the C. perfringens necrotic enteritis toxin B (NetB) (44% identical, 60% similar a.a.) to the β-toxin to C. perfringens (33% identical, 51% similar a.a.) to the cytotoxin K of Bacillus turingensis (29% identical, 48% similar a.a.) and to the α-toxin of Staphylococcus aureus (30% identical, 50% similar a.a.).

In order to study the presence and genetic structure of the cctA gene in various C. chauvoei strains including the type strain ATCC 10092$^T$ and clinical strains from Brazil, United Kingdom, Sweden and Switzerland isolated between 1965 and 2007 (Table 1), genomic DNA of these strains was used as template to amplify a 1.4 kb fragment containing cctA and its promoter and RBS using oligonucleotide primers Cct001 (CAAAATTTGGGCAGAAAAGAAG) (SEQ ID NO 7) and Cct004 (AGGATGCGTCAAC AATTTCTC) (SEQ ID NO 8). The resulting fragments that were sequenced in both directions using the same primers plus two internal primers Cct002 (GGTTATAGCATTGG TGGAAGC) (SEQ ID NO 9) and Cct003 (AAAAGCAACTTCCCAAGATGC) (SEQ ID NO 10) revealed the same nucleotide sequence as the reference strain JF4135 used for genomic sequencing with the exception of the UK strain JF3703 that contained 3 single nucleotide polymorphisms (SNP) affecting the 3$^{rd}$ that do not alter the encoded amino acid (ATT$_{Ile127}$ instead of ATC$_{Ile127}$; ACC$_{Thr129}$ instead of ACT$_{Thr129}$; TCA$_{Ser138}$ instead of TCG$_{ser138}$). Monospecific polyclonal antibodies directed against the CctA part of purified CctA:NusA reacted on standard immunoblots (as described here-above) containing 15 µl aliquots of culture supernatants of C. chauvoei of all strains (Table 1) after electrophoresis on denaturing PAGE with a 33 kDa and to a lesser extent to a band of approximately 65 kDa. In other words, each toxin in the supernatants derived from various strains is characterised in that it binds to polyclonal rabbit antibodies raised against a protein according to SEQ ID NO 1. It may be clear that the same is true for polypeptides derived from the naturally occurring toxins such as the polypeptide according to SEQ ID NO1 itself expressed in E. coli or a toxoid. Indeed, as is commonly known, other non-naturally occurring polypeptides may be devised, still having the dominant immunogenic epitopes and thus, still binding to polyclonal rabbit antibodies directed against a protein according to SEQ ID NO 1. Bio-informatics analysis of the amino-acid sequence of CctA revealed that the residues Asp149, Arg185 and Tyr187 (see SEQ ID NO 1) are involved in the membrane specificity and pore forming activity of the newly found toxin and indicates that these residues are dominant for the toxicity and hence for an adequate immune response. This corresponds to the situation with regard to Staphylococcus aureus α-toxin (Song, L. et al., 1996: "Structure of staphylococcal alpha-hemolysin, a heptameric transmembrane pore" in Science 274, 1859-1866; Walker, B. et al., 1995: "Restoration of pore-forming activity in staphylococcal alpha-hemolysin by targeted covalent modification" in Protein Eng. 8, 491-495). It is noted that when non-denaturing gels were used for the immunoblots, only the 65 kpa band was detected, showing that CctA seems to be present as a 65 kDa dimer of the 33 kDa CctA peptide, when secreted by C. chauvoei under standard growth conditions.

Hemolytic and Cytotoxic Activity of CctA

Figure 2:
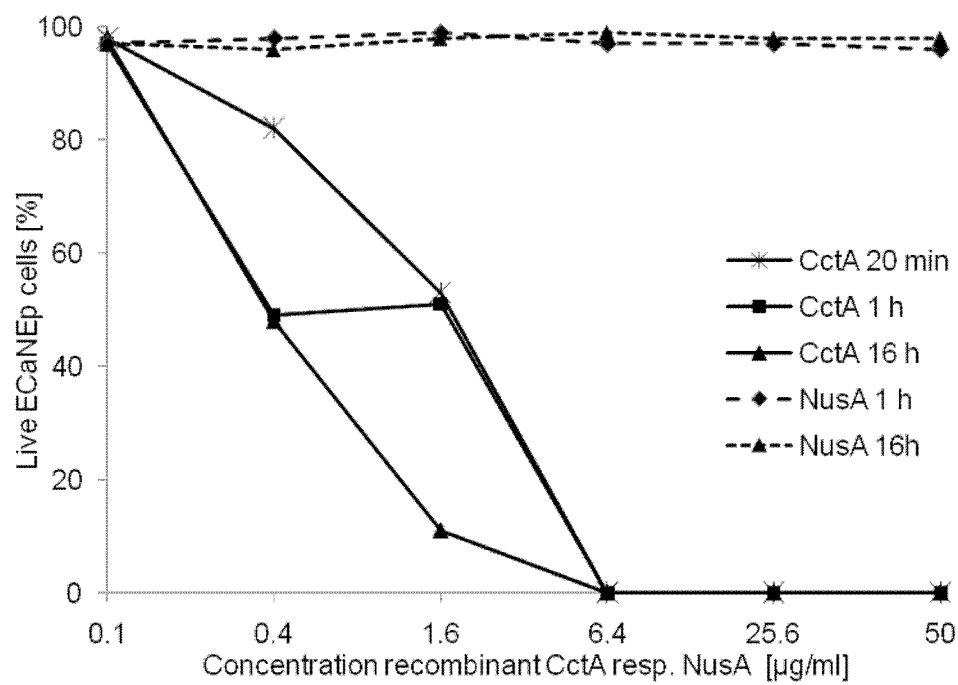

Recombinant CctA-fusion protein CctA:NusA, purified on a nickel affinity column and dialyzed against PBS buffer pH 7.5 showed strong hemolytic activity toward sheep erythrocytes both in a liquid assay with washed erythrocytes in suspension in PBS as well as on standard blood-agar bacterial growth medium. In liquid assays (Frey, J. et al., 1988, "Purification and partial characterization of a hemolysin produced by Actinobacillus pleuropneumoniae type strain 4074" in FEMS Microbiol. Lett. 55, 41-46) 50% hemolysis was obtained with recombinant CctA:NusA at a final concentration of 12.5 µg/ml and with culture supernatant at a dilution of 1:64. Recombinant NusA that was produced and purified the same way was not hemolytic. Removal of the NusA and 6×His tags from the fusion protein CctA:NusA lead to precipitation of CctA and loss of hemolytic activity. Cytotoxicity assays were therefore made using the fusion protein CctA: NusA (stock solution at 200 µg/ml) and recombinant NusA (stock solution 200 µg/ml) as a control. Analysis of surviving ECaNEp cells incubated with various concentrations of CctA:NusA for various incubation times revealed that CctA: NusA killed 50% of the cells at a concentration of 0.78 µg/ml after 1 hour incubation, longer incubations having no effect on cell mortality. CctA:NusA at a concentration of 6.4 µg/ml virtually killed almost 100% of ECaNEp cells (FIG. 1, FIG. 2). Control experiments with NusA produced and purified with the same protocol and under the same conditions showed no toxic effect on ECaNEp cells at a concentration of 50 µg/ml even after 16 h of incubation (FIG. 1). Supernatant of cultures of C. chauvoei grown anaerobically in liquid CMM under standard condition (72 H) showed 50% cytotoxicity after 1 hour incubation at a final dilution of 1:128 and 100% cytotoxicity at a dilution of 1:16 for all strains used in this study (FIG. 1; FIG. 2). The same cytotoxic potential was measured when supernatant of cultures of C. chauvoei grown under the same conditions for only 18 h or with extended growth for 7 days was used.

Neutralization of Cytotoxicity by Anti-CctA Antibodies

In order to determine to what extent the cytotoxic activity secreted by C. chauvoei is due to the toxin CctA, neutralization experiments using monospecific polyclonal antibodies directed against recombinant CctA:NusA were performed. Anti-CctA:NusA serum at a dilution of 1:32 fully neutralized the cytotoxic activity of recombinant CctA at 6.4 µg/ml (concentration giving 100% cytotoxicity towards ECaNEp cells), while pre-immunization serum from the same rabbits or serum directed against recombinant NusA had no neutralizing effect (FIG. 1). Furthermore, anti-CctA:NusA serum at a dilution of 1:32 fully neutralized the cytotoxicity of C. chauvoei culture supernatant (final dilution of 1:16, representing fully lethal dilution towards ECaNEp cells). This protective effect was found up to 16 h incubation of ECaNEp cells with C. chauvoei supernatant plus anti-CctA:NusA serum. Titration experiments with anti-CctA:NusA serum using C. chauvoei strain JF4135 supernatants diluted to 1:128 (50% cytotoxicity) with 1 h incubation time of ECaNEp cells revealed a neutralizing titer of 1:512. This serum also neutralized the hemolytic activity of C. chauvoei culture supernatants at a dilution of 1:64. Neutralization of the hemolytic activity is also observed, when the serum is applied to standard blood-agar medium plates.

Cross-Reaction with Toxin of Other *Clostridium* Bacteria

Figure 3:
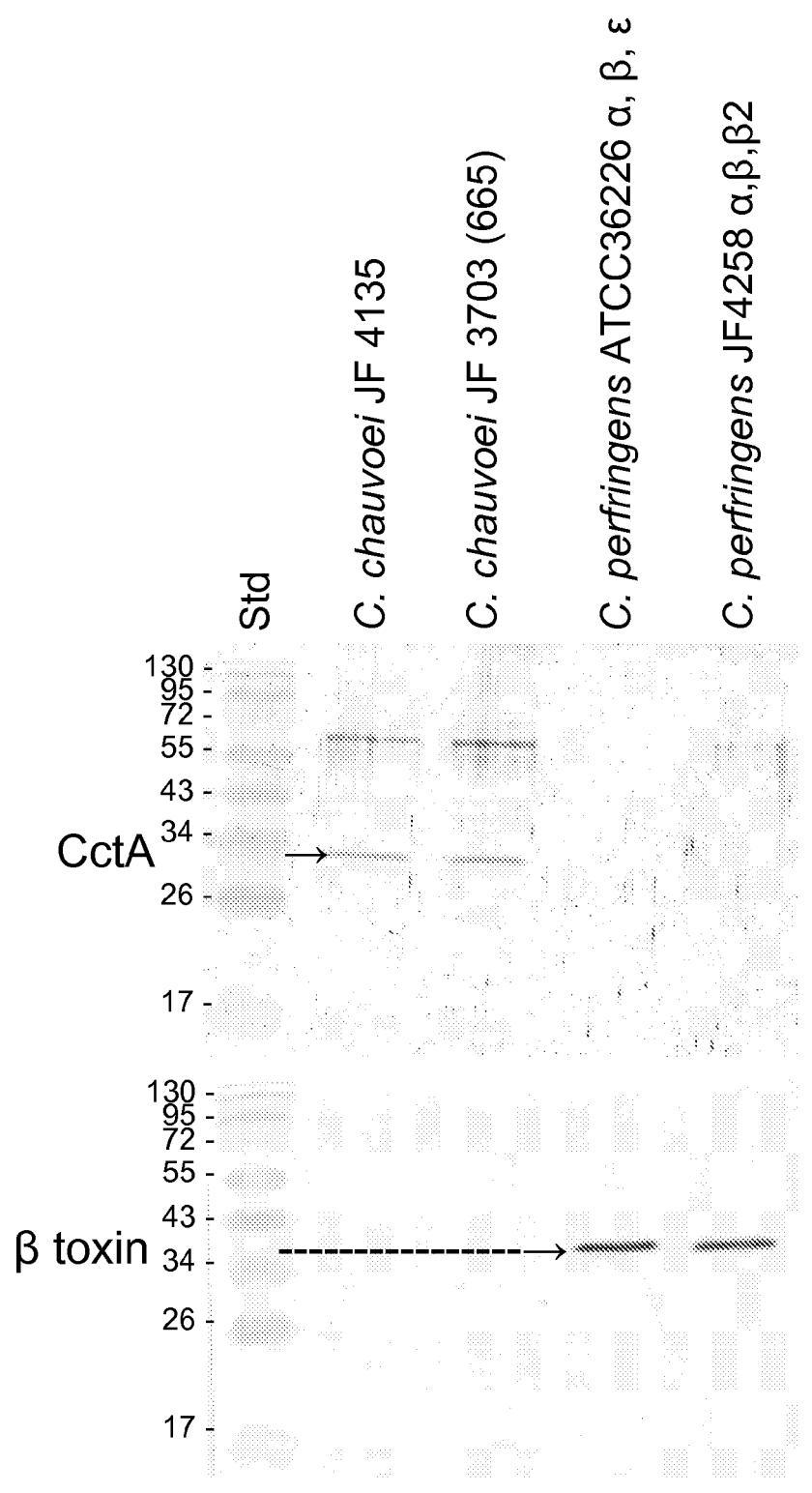

It was demonstrated that there are no cross-reactions of anti-CctA antibodies with the R-toxin of *Clostridium perfringens*. This is depicted in FIG. 3. The upper part shows an immunoblot of the supernatant of two *Clostrium chauvoei* strains and two *Clostridium perfringens* strains reacted with anti-CctA antibodies. The lower part shows an immunoblot of anti-β toxin antibodies reacted with supernatant of the same strains. It is clear that the CctA toxin is a completely new and distinct toxin. This has been confirmed by demonstrating (results not shown) that supernatant of NetB toxigenic *Clostridium perfringens* strains isolated from necrotic enteritis in chickens do not bind to polyclonal rabbit anti-CctA antibodies either.

Guinea Pig Protection Assay

In the first experiment all 5 control animals were dead or had to be euthanised within 28 hours of challenge. The first vaccinate was euthanized 44 hours after challenge, three were euthanised during the remaining 26 hours and one vaccinate survived for the whole 5 day post-challenge observation period.

In the second experiment all 5 control animals were dead or had to be euthanised within 29 hours of challenge. The first vaccinate was euthanized 44 hours after challenge, two animals were euthanised during the remaining 26 hours and two vaccinated animals survived for the whole 5 day post-challenge observation period.

CONCLUSION

The present invention is based on the identification and initial characterization of CctA, a novel, secreted toxin of *Clostridium chauvoei* that represents the major cytotoxic activity of *C. chauvoei*. Moreover, this toxin also confers *C. chauvoei* its characteristic strong hemolytic activity towards erythrocytes of various species, since anti-CctA antibodies fully neutralize hemolysis by *C. chauvoei* on standard blood-agar medium or in cell-free supernatants of liquid cultures. The gene cctA that encodes toxin is well conserved in *C. chauvoei* strains isolated from various continents collected over a period of more than 50 years from various continents and all strains tested show to express and to secrete the CctA toxin. The mature CctA seems to be secreted by *C. chauvoei* as a dimer of 65 kDa that is composed of two CctA peptides of an apparent molecular mass of 33 kDa on SDS-PAGE and that corresponds well to the calculated molecular mass of the mature peptide of 32.3 kDa. CctA is similar in molecular mass to the *C. perfringens* β-toxin (Hunter, S. E. et al., 1993: "Molecular genetic analysis of beta-toxin of *Clostridium perfringens* reveals sequence homology with alpha-toxin, gamma-toxin, and leukocidin of *Staphylococcus aureus*" in Infect. Immun. 61, 3958-3965) and NetB (Keyburn, A. L. et al., 2008: "NetB, a new toxin that is associated with avian necrotic enteritis caused by *Clostridium perfringens*" in PLoS Pathog. Volume 4, Issue 2, e26). However, the two *C. perfringens* toxins have limited sequence identity (33% and 44% identical a.a. respectively) to CctA. In the prior art, many toxins are described for *C. chauvoei*. However, since anti-CctA antibodies neutralise virtually all hemolytic activity found in *C. chauvoei* culture supernatants, other toxins seem to play a minor role in hemolysis of *C. chauvoei*. Indeed, it has been shown that a vaccine based solely on a polypepetide corresponding to CctA provided (partial) protection against a challenge with wild-type *C. chauvoei*. It is believed that the vaccine can be improved by adding a hyaluronidase or sialidase polypeptide.

The presence of a gene in *C. chauvoei* that encodes a sialidase (tentatively called the nanA gene) was demonstrated in all seven *C. chauvoei* strains used (Table 1) by PCR using the primers SiaCC_1371F (ATCAGCAATAGATACATC) (SEQ ID NO 11) and SiaCC_1789R (TGACCTCTTCCTG-GTCCTGT) (SEQ ID NO 12). PCR was carried out in 30 µl reaction mixture containing 1× reaction buffer B (supplied with FIREPol® DNA polymerase), 2.5 mM $MgCl_2$, 0.4 mM of each primer, 1 mM dNTPs, and 2.5 U of FIREPol® polymerase (Solis BioDyne, Tartu, Estonia). About 100 ng of genomic DNA was added as template. Cycling conditions on a 9800 Fast Thermal Cycler (Applied Biosystems, Foster City, Calif., USA) were 3 mM denaturation at 94° C., followed by 35 cycles at 94° C. for 30 s, 56° C. for 30 s and 72° C. for 60 s. A final extension step for 7 min at 72° C. was included. The amplicons were analysed by electrophoresis on a 1.0% agarose gel according to standard procedures.

To generate recombinant nanA, the N- and C-terminal domains (corresponding to aa position 122 772) of the NanA of *C. chauvoei* were amplified using the primers SiaCC_B-ssHIIF (TTGgcgcgcAATGATAAAAGAATACA AAATT-TATGCG) (SEQ ID NO 13) and SiaCC_HindIIIR (CCCaagcttTATAAATTTCCATTTTCTGTTA TTAAACC) (SEQ ID NO 14) (nucleotides in lower case are extensions containing recognition sites for the restriction enzymes BssHII and HindIII, respectively). The resulting PCR product was cloned into the vector T-easy (Promega, Madison, USA) and transformed into *E. coli* strain DH5α. Recombinant plasmids with correct sequence were then digested with BssHII and HindIII, and the DNA fragment was ligated into the multiple cloning site of vector pFastBac1™ digested with BssHII and HindIII (Invitrogen, La Jolla, Calif.). The pFast-bac1::nanA construct was transformed into DH5α. To ensure the correct sequence of the nanA insert, DNA sequence analysis was performed with the same primers as used for the initial sequence analysis of nanA. The sialidase activity of DH5α carrying pFastBac1::nanA and the empty vector pFastBac1 were tested as follows: The fluorogenic substrate 2'-(4-methylumbelliferyl)-α-d-N-acetylneuraminic acid (MUNeu5Ac; Sigma-Aldrich chemical, St. Louis, USA) was used to assay sialidase activity (21). A working solution of 15 µM MUNeu5Ac in 0.17 M sodium acetate buffer (pH 6.5) was prepared. Colonies of *C. chauvoei* or of recombinant *E. coli* or 10 µl of supernatant from liquid *C. chauvoei* cultures were spotted onto filter paper (1 MM, Whatman) that was previously moistened with the MUNeu5Ac solution (15 µM MUNeu5Ac in 0.17 M sodium acetate buffer) and then incubated at 37° C. for 15 min. The reactions were stopped (0.085 M glycine, 0.2 M sodium carbonate, pH 9.4), the filter papers air-dried and fluorescence observed under a UV light (wavelength, 360 nm). Observable bright blue fluorescence was recorded as positive.

This way it was found that the full length *C. chauvoei* sialidase gene nanA consists of 2319 bp. A ribosome binding site (AGGTGG) is found 8 bases upstream of the start codon ATG and is preceded by a characteristic promoter sequence including TATA box (TATAAA) and a −35 element (TT-TACA). The protein derived from the nucleotide sequence consists of 772 aa, with a predicted molecular mass of 83.9 kDa and pI of 4.96. The aa sequence derived from the DNA sequence reveals a leader sequence peptidase cleavage site between position 26 and 27 (IlePheAla↓AspIle) that is characteristic for secreted proteins of Gram-positive bacteria. The putative mature sialidase consists of 746 aa with a calculated molecular mass of 81 kDa. A full report of this information has been submitted as a paper to the Journal of Bacteriology (Anders Johansson, Edy M. Vilei, Keith Redhead, Joachim Frey: "Genetic and functional characterization of the NanA sialidase from *Clostridium chauvoei*").

FIGURE LEGENDS

FIG. 1
Cytotoxicity and neutralization assay using Embryonic Calf Nasal Epithelial (ECaNEp) cells. A: untreated cells; B: incubated 1 h with 6.4 μg/ml recombinant CctA:NusA; C: incubated 16 h with 50 μg/ml recombinant NusA; D: incubated 1 h with 6.4 μg/ml CctA:NusA pretreated with rabbit anti-CctA:NusA serum diluted 1:32; E: incubated 1 h with culture supernatant of *C. chauvoei* strain JF4135 diluted 1:16: F: incubated 1 h with culture supernatant of *C. chauvoei* strain JF4135 pretreated with rabbit anti-CctA:NusA serum diluted 1:32.

FIG. 2
Cytotoxicity assay using ECaNEp cells. ECaNEp cells were treated with different concentrations of recombinant CctA:NusA or with recombinant NusA as a control. The horizontal axis represents the concentration of recombinant CctA fusion protein and NusA respectively in μg/ml. The vertical axis represents the percentage of live ECaNEp cells. The data are mean values from 3 different wells. Live ECaNEp cells were counted in all wells and given in % of lives cells in the untreated wells at the beginning of the experiment.

FIG. 3
Immunoblots of supernatants of two *Clostridium chauvoei* strains and two *Clostridium perfringens* strains with anti-CctA antibodies (upper part) and anti-β toxin antibodies (lower part).

The invention claimed is:

1. An isolated polypeptide comprising the amino acid sequence of SEQ ID NO 1 that is expressed recombinantly.

2. An immunogenic composition comprising the polypeptide of claim 1 and a pharmaceutically acceptable carrier.

3. An isolated polypeptide comprising the amino acid sequence of SEQ ID NO 1.

4. An immunogenic composition comprising the polypeptide of claim 3 and a pharmaceutically acceptable carrier.

5. An isolated polypeptide consisting of the amino acid sequence of SEQ ID NO 1.

* * * * *

SEQUENCE LISTING

```
<160> NUMBER OF SEQ ID NOS: 4

<210> SEQ ID NO 1
<211> LENGTH: 278
<212> TYPE: PRT
<213> ORGANISM: Clostridium chauvoei

<400> SEQUENCE: 1

Ser Glu Gly Val Lys Thr Phe Thr Ser Ser Asp Thr Ala Tyr Ala Asp
1               5                   10                  15

Tyr Asn Cys Phe Lys Thr Asn Leu Ser Val Thr Phe Ile Glu Asp Gln
                20                  25                  30

His Asn Asn Gln Leu Thr Ala Leu Val Ser Thr Glu Gly Ser Phe Ile
            35                  40                  45

Pro Ser Gly Leu Ser Arg Val Gly Gly Tyr Tyr Gln Ala Asp Met Tyr
        50                  55                  60

Trp Pro Ser Lys Tyr Tyr Thr Thr Leu Thr Thr Tyr Asp Arg Asn Asn
65                  70                  75                  80

Arg Val Lys Ile Thr Lys Ser Ile Pro Thr Asn Gln Ile Asp Thr Val
                85                  90                  95

Ser Val Ser Glu Thr Met Gly Tyr Ser Ile Gly Gly Ser Leu Ser Ile
            100                 105                 110

Glu Tyr Gly Lys Glu Gly Pro Lys Ala Gly Gly Gly Ile Asn Gly Ser
        115                 120                 125

Tyr Thr Ala Gln Arg Ser Val Thr Tyr Asp Gln Pro Asp Tyr Arg Thr
130                 135                 140

Leu Leu Met Lys Asp Ser Val Asn Ser Ala Ser Trp Glu Val Ala Phe
145                 150                 155                 160

Asn Ala Thr Lys Asp Gly Tyr Asp Arg Asp Ser Tyr His Gly Ile Tyr
                165                 170                 175

Gly Asn Gln Leu Phe Met Arg Tyr Arg Leu Tyr Asn Thr Gly Ile Asn
            180                 185                 190

Asn Leu Thr Thr Asp Asn Asn Leu Ser Ser Leu Ile Val Gly Gly Phe
        195                 200                 205

Ser Pro Lys Val Val Ile Ala Leu Thr Ala Pro Lys Gly Thr Glu Glu
    210                 215                 220

Ser Thr Val Lys Val Glu Tyr Asn Arg Phe Asn Asp Gln Tyr Arg Leu
225                 230                 235                 240

Arg Trp Ser Gly Thr Glu Trp Tyr Gly Glu Asn Asn Arg Asn Ser Arg
                245                 250                 255
```

```
Ile Asp Ser Ser Ser Glu Ser Phe Ile Leu Asn Trp Lys Asn His Thr
            260                 265                 270

Val Glu His Ala Gly Tyr
            275

<210> SEQ ID NO 2
<211> LENGTH: 317
<212> TYPE: PRT
<213> ORGANISM: Clostridium chauvoei

<400> SEQUENCE: 2

Met Ile Lys Arg Ile Leu Met Leu Ala Leu Ala Thr Thr Thr Ile Phe
1               5                   10                  15

Ser Leu Thr Leu Pro Phe Ser Tyr Lys Ala Val Gln Ala Gln Glu Asn
            20                  25                  30

Thr Cys Ile Val Glu Thr Pro Ser Glu Gly Val Lys Thr Phe Thr Ser
        35                  40                  45

Ser Asp Thr Ala Tyr Ala Asp Tyr Asn Cys Phe Lys Thr Asn Leu Ser
    50                  55                  60

Val Thr Phe Ile Glu Asp Gln His Asn Gln Leu Thr Ala Leu Val
65                  70                  75                  80

Ser Thr Glu Gly Ser Phe Ile Pro Ser Gly Leu Ser Arg Val Gly Gly
                85                  90                  95

Tyr Tyr Gln Ala Asp Met Tyr Trp Pro Ser Lys Tyr Tyr Thr Thr Leu
            100                 105                 110

Thr Thr Tyr Asp Arg Asn Asn Arg Val Lys Ile Thr Lys Ser Ile Pro
        115                 120                 125

Thr Asn Gln Ile Asp Thr Val Ser Val Ser Glu Thr Met Gly Tyr Ser
    130                 135                 140

Ile Gly Gly Ser Leu Ser Ile Glu Tyr Gly Lys Glu Gly Pro Lys Ala
145                 150                 155                 160

Gly Gly Gly Ile Asn Gly Ser Tyr Thr Ala Gln Arg Ser Val Thr Tyr
                165                 170                 175

Asp Gln Pro Asp Tyr Arg Thr Leu Leu Met Lys Asp Ser Val Asn Ser
            180                 185                 190

Ala Ser Trp Glu Val Ala Phe Asn Ala Thr Lys Asp Gly Tyr Asp Arg
        195                 200                 205

Asp Ser Tyr His Gly Ile Tyr Gly Asn Gln Leu Phe Met Arg Tyr Arg
    210                 215                 220

Leu Tyr Asn Thr Gly Ile Asn Asn Leu Thr Thr Asp Asn Asn Leu Ser
225                 230                 235                 240

Ser Leu Ile Val Gly Gly Phe Ser Pro Lys Val Val Ile Ala Leu Thr
                245                 250                 255

Ala Pro Lys Gly Thr Glu Glu Ser Thr Val Lys Val Glu Tyr Asn Arg
            260                 265                 270

Phe Asn Asp Gln Tyr Arg Leu Arg Trp Ser Gly Thr Glu Trp Tyr Gly
        275                 280                 285

Glu Asn Asn Arg Asn Ser Arg Ile Asp Ser Ser Glu Ser Phe Ile
    290                 295                 300

Leu Asn Trp Lys Asn His Thr Val Glu His Ala Gly Tyr
305                 310                 315

<210> SEQ ID NO 3
<211> LENGTH: 834
<212> TYPE: DNA
<213> ORGANISM: Clostridium chauvoei
```

<400> SEQUENCE: 3

```
agtgaaggag taaagacttt tacatcttca gatactgctt atgcagatta taattgcttt       60
aagactaact tatcagttac atttattgaa gatcaacaca ataatcaact tacagcactt      120
gtatcaacag aaggatcatt tattccatca ggattatcac gtgttggtgg gtattatcaa      180
gctgatatgt attggccatc aaaatattac acaacattaa caacttatga tagaaataat      240
agagtaaaaa taactaaaag tatcccaact aatcaaatag atacagtatc agtatcggaa      300
actatgggtt atagcattgg tggaagctta tcaattgaat atggaaaaga aggccctaaa      360 gcaggggag gaataaatgg atcatacact gctcaaagaa gtgtaacata tgatcaacca      420
gattatagaa cattattaat gaaagatagt gtaaatagtg catcttggga agttgctttt      480
aatgcaacta aagatggata tgatagagat tcttatcatg gtatctatgg aaatcaatta      540
tttatgagat atagattata aatacagga ataaataatt aactacaga taacaattta      600 tcttctttaa tagttggtgg tttttctcct aaagtagtaa ttgctcttac agcaccaaaa      660
ggaactgaag aatcaacagt taaagttgaa tataatcgtt ttaatgatca atatagatta      720
agatggtcag gaactgaatg gtatggagaa aataatagaa attctagaat agatagttca      780
agtgagtctt tcatacttaa ttggaaaaac catactgttg agcatgcagg atat           834
```

<210> SEQ ID NO 4
<211> LENGTH: 1420
<212> TYPE: DNA
<213> ORGANISM: Clostridium chauvoei

<400> SEQUENCE: 4

```
caaaatttgg gcagaaaaga agaaaaataa aattataata aatattaaat ggaatttata       60
accataaaaa tgagtgtata tttgaatata tactcatttt tttatgtaaa taaaaagaat      120
tttaataaaa aaattaaaaa aattaaataa aagtgtaaaa aaagtacttt gattataaaa      180
atatattcaa aaaatattga aaatatgtta atataatatt aacaataagt aaacgtttat      240
gagttgttta tactaattaa tataaaatgg ggagggacaa tatgataaaa agaatattaa      300
tgcttgcttt agcaacaaca actatattta gcttaacttt acctttttcc tataaagctg      360
tacaagctca agaaaataca tgtatagttg aaacaccaag tgaaggagta aagacttta      420 catcttcaga tactgcttat gcagattata attgctttaa gactaactta tcagttacat      480
ttattgaaga tcaacacaat aatcaactta cagcacttgt atcaacagaa ggatcattta      540
ttccatcagg attatcacgt gttggtgggt attatcaagc tgatatgtat tggccatcaa      600
aatattacac aacattaaca acttatgata gaaataatag agtaaaaata actaaaagta      660
tcccaactaa tcaaatagat acagtatcag tatcggaaac tatgggttat agcattggtg      720
gaagcttatc aattgaatat ggaaaagaag gccctaaagc aggggagga ataaatggat      780 catacactgc tcaaagaagt gtaacatatg atcaaccaga ttatagaaca ttattaatga      840 agatagtgt aaatagtgca tcttgggaag ttgctttaa tgcaactaaa gatggatatg      900
atagagattc ttatcatggt atctatggaa atcaattatt tatgagatat agattatata      960
atacaggaat aaaatttta actacagata caatttatc ttctttaata gttggtggtt     1020
tttctcctaa agtagtaatt gctcttacag caccaaaagg aactgaagaa tcaacagtta     1080
aagttgaata taatcgtttt aatgatcaat atagattaag atggtcagga actgaatggt     1140
atggagaaaa taatagaaat tctagaatag atagttcaag tgagtctttc atacttaatt     1200
ggaaaaacca tactgttgag catgcaggat attaatacat aaatcaaaaa gctatagatc     1260
```

```
tttaataggt ctatagcttt ttatttataa ttaattcagt tcattttcta atttagaaat    1320
tgactcatca aatatctcaa catttctagc ttgaatatct atgttagcag caatttcttc    1380
acatagagct gtgtgttctt gagaaattgt tgacgcatcc                          1420
```